United States Patent
Packard

(10) Patent No.: US 7,435,600 B2
(45) Date of Patent: Oct. 14, 2008

(54) INFRARED METHODS OF MEASURING THE EXTENT OF CURE OF A BINDER IN FIBROUS PRODUCTS

(75) Inventor: Richard Thomas Packard, Elbert, CO (US)

(73) Assignee: Johns Manville, Denver, CO (US)

(*) Notice: Subject to any disclaimer, the term of this patent is extended or adjusted under 35 U.S.C. 154(b) by 906 days.

(21) Appl. No.: 10/874,671

(22) Filed: Jun. 23, 2004

(65) Prior Publication Data
US 2005/0287675 A1    Dec. 29, 2005

(51) Int. Cl.
*G01N 33/44* (2006.01)
(52) U.S. Cl. .................. 436/85; 436/128; 436/129; 436/171
(58) Field of Classification Search .............. 436/85, 436/127–129, 164, 171
See application file for complete search history.

(56) References Cited

U.S. PATENT DOCUMENTS

| | | | |
|---|---|---|---|
| 3,524,983 A | 8/1970 | Voelz | |
| 4,363,968 A | 12/1982 | McGowan et al. | |
| 4,582,520 A | 4/1986 | Sturm | |
| 4,609,628 A | 9/1986 | Aschenbeck | |
| 4,767,804 A * | 8/1988 | Willoughby | 523/351 |
| 4,769,544 A | 9/1988 | Dahlquist | |
| 4,798,954 A | 1/1989 | Stevenson | |
| 4,975,300 A * | 12/1990 | Deviny | 427/509 |
| RE33,789 E | 1/1992 | Stevenson | |
| 5,142,151 A | 8/1992 | Varnell et al. | |
| 5,367,027 A * | 11/1994 | Fushimi et al. | 525/208 |
| 5,457,319 A | 10/1995 | Moe et al. | |
| 5,534,612 A * | 7/1996 | Taylor et al. | 528/129 |
| 5,668,210 A * | 9/1997 | Harris et al. | 524/588 |
| 5,719,228 A * | 2/1998 | Taylor et al. | 524/593 |
| 5,932,665 A * | 8/1999 | DePorter et al. | 525/381 |
| 6,130,980 A * | 10/2000 | Murphy et al. | 385/115 |
| 6,410,647 B1 * | 6/2002 | Yoshioka et al. | 525/166 |
| 7,001,528 B2 * | 2/2006 | Laubender et al. | 210/777 |
| 7,043,326 B2 * | 5/2006 | Neubauer et al. | 700/117 |
| 2003/0024527 A1 | 2/2003 | Ginn | |
| 2003/0074095 A1 | 4/2003 | Neubauer et al. | |

* cited by examiner

*Primary Examiner*—Arlen Soderquist
(74) *Attorney, Agent, or Firm*—Robert D. Touslee

(57) ABSTRACT

A method of measuring the extent of cure of a binder in a fibrous product is provided. The method comprises (a) providing a sample of a fibrous product, the fibrous product comprising fibers and a binder, (b) subjecting the sample to infrared spectroscopy to generate a spectral analysis, and (c) determining a binder cure ratio of the binder in the sample using the spectral analysis. The binder has carboxylic acid groups and alcohol groups that crosslink to form ester groups as the binder cures, and the binder cure ratio comprises a ratio between infrared absorption corresponding to a bond of the carboxylic acid groups in the binder and infrared absorption corresponding to a bond of the ester groups in the binder.

38 Claims, 3 Drawing Sheets

INFRARED METHODS OF MEASURING THE EXTENT OF CURE OF A BINDER IN FIBROUS PRODUCTS

FIELD

The present invention generally relates to methods of measuring the cure of a binder in fibrous products.

BACKGROUND

Different binder systems have been used in the manufacture of fiberglass insulation, including phenolic-based binders and polycarboxylic acid binders. The use of phenolic-based binders allows the extent of curing of the binder system to be judged by visual observation, as the appearance of the fiberglass changes as the binder cures. The use of polycarboxylic acid binders such as polyacrylic acid binders, however, does not allow the extent of curing of the binder to be judged by visual observation, as fiberglass insulation manufactured with polycarboxylic acid binder maintains the same or a similar appearance regardless of the extent of cure of the binder.

Fiberglass insulation with binder that is insufficiently cured exhibits poor mechanical performance. Therefore, it would be desirable to provide a method of determining the degree of cure of fibrous products such as fiberglass insulation that include a polycarboxylic acid binder such as a polyacrylic acid binder.

SUMMARY

In one aspect, a method of measuring the extent of cure of a binder in a fibrous product is provided. The method comprises (a) providing a sample of a fibrous product, the fibrous product comprising fibers and a binder, (b) subjecting the sample to infrared spectroscopy to generate a spectral analysis, and (c) determining a binder cure ratio of the binder in the sample using the spectral analysis. The binder has carboxylic acid groups and alcohol groups that crosslink to form ester groups as the binder cures, and the binder cure ratio comprises a ratio between infrared absorption corresponding to a bond of the carboxylic acid groups in the binder and infrared absorption corresponding to a bond of the ester groups in the binder. The binder cure ratio that is determined is indicative of the extent of cure of the binder in the fibrous product.

In another aspect, another method of measuring the extent of cure of a binder in a fibrous product is provided. The method comprises (a) providing a sample of a fibrous product, the fibrous product comprising fibers and a binder, (b) subjecting the sample to infrared spectroscopy to generate a spectral analysis, (c) determining a binder cure ratio of the binder in the sample using the spectral analysis, (d) determining a neutralization ratio of the binder in the sample using the spectral analysis, and (e) using the binder cure ratio and the neutralization ratio to determine the extent of cure of the binder in the fibrous product. The binder has carboxylic acid and alcohol groups that crosslink to form ester groups as the binder cures, and the binder is capable of being neutralized to an acid salt having a carboxylate group. The binder cure ratio comprises a ratio between infrared absorption corresponding to a bond of the carboxylic acid groups in the binder and infrared absorption corresponding to a bond of the ester groups in the binder. The neutralization ratio comprises a ratio between infrared absorption corresponding to a bond of the carboxylate groups in the acid salt of the binder and total infrared absorption corresponding to a bond of the carboxylic acid groups in the binder and a bond of the ester groups in the binder.

In a further aspect, yet another method of measuring the extent of cure of a binder in a fibrous product is provided. The method comprises:

(a) providing a sample of a fibrous product, the fibrous product comprising fibers and a binder, the binder having carboxylic acid and alcohol groups that crosslink to form ester groups as the binder cures, the binder capable of being neutralized to an acid salt having a carboxylate group, the binder also capable of forming an anhydride having a carboxylic acid anhydride group;

(b) subjecting the sample to infrared spectroscopy to generate a spectral analysis;

(c) determining a binder cure ratio of the binder in the sample using the spectral analysis, the binder cure ratio comprising a ratio between infrared absorption corresponding to a bond of the carboxylic acid groups in the binder and infrared absorption corresponding to a bond of the ester groups in the binder;

(d) determining a neutralization ratio of the binder in the sample using the spectral analysis, the neutralization ratio comprising a ratio between infrared absorption corresponding to a bond of the carboxylate groups in the acid salt of the binder and total infrared absorption corresponding to a bond of the carboxylic acid groups in the binder and a bond of the ester groups in the binder;

(e) determining an anhydride ratio of the binder in the sample using the spectral analysis, the anhydride ratio comprising a ratio between infrared absorption corresponding to a bond in the carboxylic acid anhydride groups of the anhydride of the binder and total infrared absorption corresponding to a bond of the carboxylic acid groups in the binder and a bond of the ester groups in the binder; and (f) using the binder cure ratio, the neutralization ratio, and the anhydride ratio to determine the extent of cure of the binder in the fibrous product.

In yet another aspect, a method of measuring the extent of cure of a binder in a fiberglass insulation product is provided. The method comprises: (a) providing a sample of a fiberglass insulation product, the product comprising glass fibers and a binder, (b) subjecting the sample to Fourier transform infrared spectroscopy to generate a spectral analysis, and (c) determining a binder cure ratio of the binder in the sample using the spectral analysis. The binder comprises a polyacrylic acid with carboxylic acid groups and a polyol with alcohol groups, with the carboxylic acid groups and the alcohol groups crosslinking to form ester groups as the binder cures. The binder cure ratio comprises a ratio between infrared absorption corresponding to the $C=O$ bond of the carboxylic acid groups in the binder and infrared absorption corresponding to the $C=O$ bond of the ester groups in the binder. The binder cure ratio that is determined is indicative of the extent of cure of the binder in the fiberglass insulation product.

BRIEF DESCRIPTION OF THE DRAWINGS

FIG. 1 shows the spectrum with the absorption frequencies and baseline used to calculate a binder cure ratio of the binder in the fiberglass. FIG. 2 shows the spectrum with the absorption frequencies and baselines used to calculate a neutralization ratio of the binder in the fiberglass. FIG. 3 shows the spectrum with the absorption frequencies and baseline used to calculate an anhydride ratio of the binder in the fiberglass.

DETAILED DESCRIPTION

Figure 1:
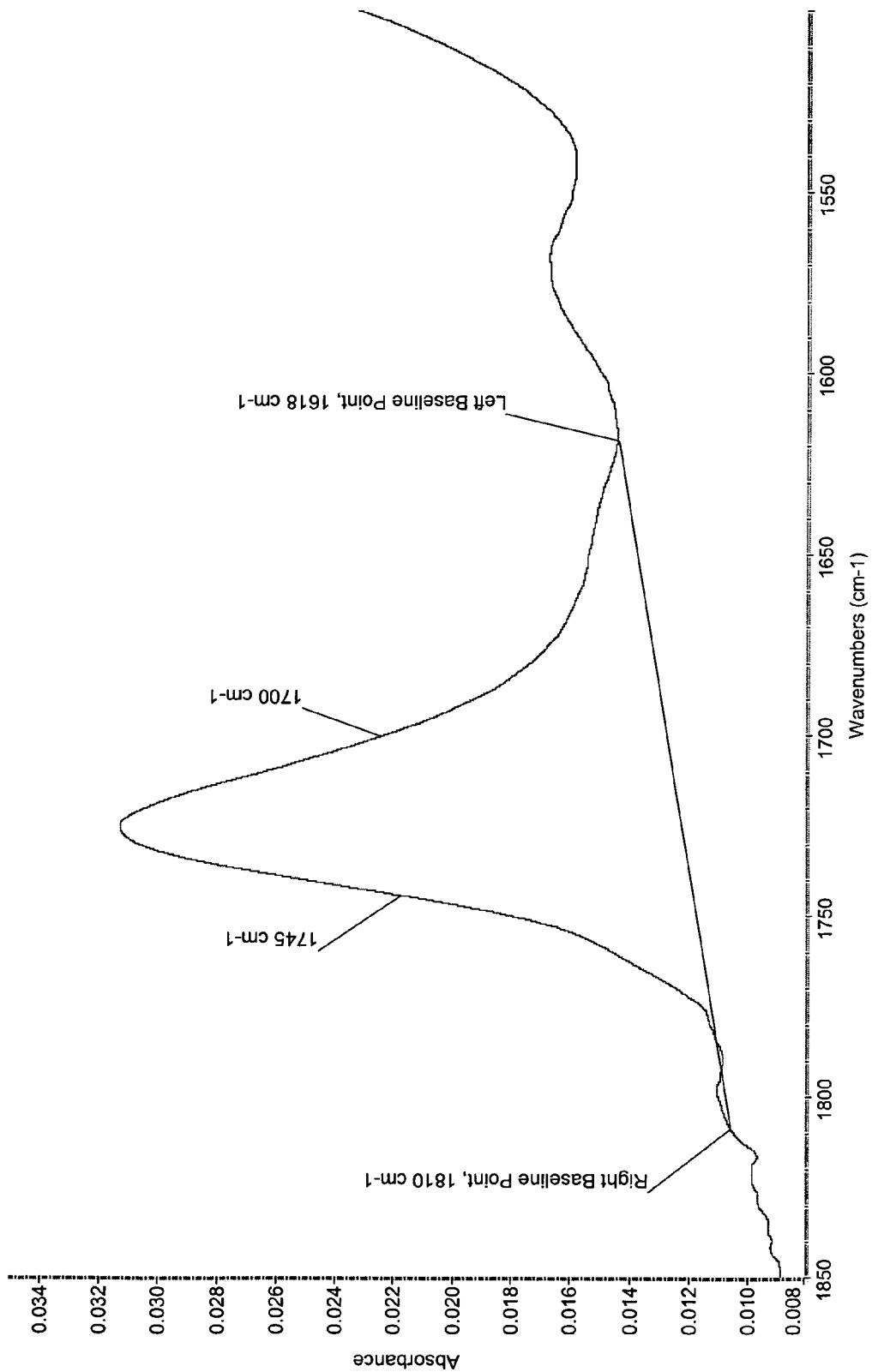
FIGS. 1-3 illustrate a Fourier transform infrared spectrum of a sample of manufactured fiberglass insulation.

The present invention relates to methods of measuring the extent of cure of a binder in fibrous products as well as methods of monitoring and adjusting the extent of cure in a manufacturing process for fibrous products. The fibrous products whose binder cure is to be measured comprise fibers and a binder, and typically include products made from various types of glass fibers such as, for example, fiberglass building insulation and nonwoven glass mats. However, the methods may be used with fibrous products made with other fibers such as, for example, mineral fibers.

The binder of the fibrous products may be any binder with carboxylic acid groups and alcohol groups that crosslink to form ester groups as the binder cures. As used herein, the term "binder" includes binders that are single compounds as well as binders that comprise multiple compounds or components (i.e., a binder system). Binders comprising single compounds contain both carboxylic acid and alcohol groups such that the compounds will self-crosslink. Binders comprising multiple compounds or components (i.e., binder systems) include more than one compound that together contain carboxylic acid and alcohol groups such that the system will crosslink. Binder systems that may be used include those with polycarboxylic acid compounds as a first component and polyol compounds as a second component such as, for example, a binder system with a polyacrylic acid and a polyol (e.g., triethanol amine). The binder may be comprised of any polycarboxylic acid compound or polyacrylic acid compound that crosslinks with alcohol groups.

Fibrous products made from fibers and binder may be produced according to known methods. For example, there are many known methods of producing fibrous products such as fiberglass insulation and glass mats. In general, the fibers are formed into a network (e.g., a mat) and binder is applied to the network. Various methods are known for forming networks of fibers as well as applying binder to such networks. Typically, the fibrous products are then subjected to a curing oven in order to heat the products and cure the binder to form the finished products. The binder in the fibrous products cures via a crosslinking reaction of the alcohol and carboxylic acid groups to form ester groups. As described more fully below, various parameters of the manufacturing process may be adjusted based on the extent of cure determined using the methods described herein in order to, for example, optimize the cure of the binder.

In the methods of measuring the extent of cure of the binder in the fibrous products, a sample of a fibrous product is first provided. The sample may be provided from a fibrous product at any stage of a manufacturing process such as, for example, a fibrous product before curing, a fibrous product in a curing oven, or a fibrous product after being heated in a curing oven. Samples of fibrous products are preferably taken shortly after completion of the manufacturing process, as the binder state may fluctuate after completion of manufacture (e.g., the binder may hydrolyze after manufacture). Therefore, if a sample is taken after manufacture of a fibrous product, the sample is typically taken as soon as possible after the manufacture of the product, for example, within 2 hours of completion, preferably within 1 hour of completion, more preferably within ½ hour of completion, although the sample may be taken at any point after manufacture, including at times longer than 2 hours after completion.

After a sample of a fibrous product is obtained, the sample is subjected to infrared spectroscopy to generate a spectral analysis (e.g., an infrared absorption spectrum). Preferably, Fourier transform infrared spectroscopy (FTIR) is used to generate the spectral analysis; however, other infrared spectroscopy techniques may also be used to generate the spectral analysis. As described below, the spectral analysis allows the calculation of one or more ratios that are indicative of and/or that may be used to determine the extent of cure of the binder in the fibrous product. Any infrared spectrometer may be used in the methods, and various sampling devices may be used with the infrared spectrometer, such as, for example, an attenuated total reflectance sampling device. In addition, the sample may be prepared for infrared spectroscopy in various ways, such as, for example, grinding the sample such that it is homogenized before being subjected to infrared spectroscopy.

After a spectral analysis has been acquired using infrared spectroscopy, the spectral analysis is used to calculate one or more ratios that are indicative of and/or allow the determination of the extent of cure of the binder. The ratios that may be calculated include a binder cure ratio, a neutralization ratio, and an anhydride ratio. The neutralization ratio may be useful for binders that are capable of being neutralized to an acid salt having a carboxylate group, and the anhydride ratio may be useful for binders that are capable of forming an anhydride having a carboxylic acid anhydride group (i.e., —C(O)—O—C(O)—).

The binder cure ratio comprises a ratio between infrared absorption corresponding to a bond of the carboxylic acid groups in the binder and infrared absorption corresponding to a bond of the ester groups in the binder, which could be expressed as acid/ester or ester/acid. As stated above, the carboxylic acid groups in the binder react (i.e., crosslink) with alcohol groups to form ester groups in the binder as the binder cures. Therefore, the binder cure ratio is a ratio between the amount of infrared absorption due to a bond in the uncrosslinked acid groups that react with the alcohol groups as the binder cures and the amount of infrared absorption due to a bond in the ester groups that are formed as the binder crosslinks/cures. Thus, the binder cure ratio is indicative of the extent of cure of the binder.

The bonds used to determine the binder cure ratio may vary, and the bonds may be chosen such that the absorption due to the binder, the fibers, and any other components in a particular fibrous product do not interfere (or do not substantially interfere) with the determination of the binder cure ratio. In one embodiment, the binder cure ratio is measured as a ratio between infrared absorption corresponding to the carbonyl (i.e., C=O) of the carboxylic acid group in the binder and infrared absorption corresponding to the carbonyl of the ester group in the binder. Absorption frequencies for the C=O bond in a carboxylic acid group of a binder are typically 1725-1700 cm$^{-1}$, although these values may vary. Absorption frequencies for the C=O bond in an ester group of a binder is typically 1750-1725 cm$^{-1}$, although these values may also vary.

The neutralization ratio comprises a ratio between infrared absorption corresponding to a bond of the carboxylate groups in the acid salt of the binder and total infrared absorption corresponding to a bond of the carboxylic acid groups in the binder and a bond of the ester groups in the binder. Therefore, the neutralization ratio comprises a ratio between the amount of infrared absorption due to a functional group representative of neutralized binder and the amount of total infrared absorption due to certain functional groups representative of total non-neutralized binder. The neutralization ratio could be expressed as neutralized/non-neutralized or non-neutralized/neutralized.

The bonds used to determine the neutralization ratio may vary, and the bonds may be chosen such that the absorption due to the binder, the fibers, and any other components in a particular fibrous product do not interfere (or do not substantially interfere) with the determination of the neutralization ratio. In one embodiment, the neutralization ratio is measured as a ratio between infrared absorption corresponding to the carbonyl (i.e., C=O) of the carboxylate group (i.e., the carboxylic acid salt group) in the acid salt of the binder and total infrared absorption corresponding to the carbonyl (i.e., C=O) of the carboxylic acid group in the binder and to the carbonyl of the ester group in the binder. As stated above, absorption frequencies for the C=O bond in a carboxylic acid group of a binder are typically 1725-1700 $cm^{-1}$ and absorption frequencies for the C=O bond in an ester group of a binder is typically 1750-1725 $cm^{-1}$, although these values may vary. Absorption frequencies for the C=O bond in the carboxylate group of an acid salt of the binder are typically 1610-1550 $cm^{-1}$, although these values may also vary.

Although not wishing to be bound by theory, it is believed that when formed in the fibrous product, acid salts of the binder interfere with the binder's ability to cure, as the acid salts are believed to reduce the ability to crosslink. Therefore, the neutralization ratio may be considered in conjunction with the binder cure ratio when determining the extent of cure of the binder.

The anhydride ratio comprises a ratio between infrared absorption corresponding to a bond of the carboxylic acid anhydride groups of the anhydride of the binder and total infrared absorption corresponding to a bond of the carboxylic acid groups in the binder and a bond of the ester groups in the binder. Therefore, the anhydride ratio represents a ratio between the amount of infrared absorption due to a functional group representative of anhydride binder and the amount of total infrared absorption due to certain functional groups representative of non-anhydride binder. The anhydride ratio could be expressed as anhydride/non-anhydride or non-anhydride/anhydride.

The bonds used to determine the anhydride ratio may vary, and the bonds may be chosen such that the absorption due to the binder, the fibers, and any other components in a particular fibrous product do not interfere (or do not substantially interfere) with the determination of the anhydride ratio. In one embodiment, the anhydride ratio is measured as a ratio between infrared absorption corresponding to the carbonyl (i.e., C=O) of the carboxylic acid anhydride groups in the anhydride of the binder and total absorption corresponding to the carbonyl (i.e., C=O) of the carboxylic acid group in the binder and to the carbonyl of the ester group in the binder. As stated above, absorption frequencies for the C=O bond in a carboxylic acid group of a binder are typically 1725-1700 $cm^{-1}$ and absorption frequencies for the C=O bond in an ester group of a binder are typically 1750-1725 $cm^{-1}$, although these values may vary. Absorption frequencies for the C=O bond in the carboxylic acid anhydride group of the anhydride binder are typically 1850-1800 and 1790-1740 $cm^{-1}$, although these values may also vary.

Although not wishing to be bound by theory, low anhydride levels present in the fibrous product are believed to be an indicator of potentially undercured product. This is because anhydride levels appear to be somewhat connected to the temperature used in the curing oven. Therefore, the anhydride ratio may be considered in conjunction with the binder cure ratio when determining the extent of cure of the binder.

The infrared absorption corresponding to the bonds used for determining each of the ratios may be measured in various ways. For example, the infrared absorption of the bonds may be measured using the absorption peak or band heights (i.e., absorbance), an area under representative absorption peaks, and/or other methods of determining or resolving the amount of infrared absorption for specific bonds that are representative of particular functional groups. In addition, the determined values may be normalized to, for example, a baseline value. Furthermore, it may be possible to determine an actual percentage for the extent of cure, the extent of neutralization, and the level of anhydride based, respectively, on the binder cure ratio, the neutralization ratio, and the anhydride ratio.

After one or more of the binder cure ratio, the neutralization ratio, and the anhydride ratio are calculated, one or more of the values are used to determine the extent of cure of the binder in the fibrous product. Typically, at least the binder cure ratio is used with or without the neutralization and anhydride ratios to determine the extent of cure of the binder in the fibrous product.

As the binder cure ratio is indicative of the extent of cure of a particular binder in a fibrous product, the binder cure ratio may be used alone to measure the extent of cure of the binder in the fibrous product. For example, the binder cure ratio may be compared to a predetermined scale to gauge the extent of cure of the binder. Such a predetermined scale may be tailored for a specific binder and/or a specific fibrous product. In addition, as discussed above, it may also be possible to determine an actual percentage for the extent of cure based on the binder cure ratio that may be used to gauge the extent of cure of the binder.

One or both of the neutralization and anhydride ratios may also be used as supplements to the binder cure ratio to aid in determining the extent of cure of the binder in the fibrous products. One or both of the neutralization and anhydride ratios may be compared to a predetermined scale or scales (along with the binder cure ratio) to determine the extent of cure of the binder. In addition, it may be possible to combine the binder cure ratio with one or both of the neutralization and anhydride ratios in order to determine the extent of cure of the binder in the fibrous products using only one predetermined scale or mathematical equation.

After determining the extent of cure of the binder in the fibrous product, various parameters of the manufacturing process may be adjusted to achieve a more desired extent of cure of the binder in the fibrous products produced by the manufacturing process. For example, the parameters of the curing oven (e.g., time in curing oven, temperature of oven, moisture level in oven, air flow in oven, etc.) and the pH of the binder may be adjusted to achieve a more desired extent of cure of the binder. Such adjustments may be useful when the sample of fibrous product is obtained at any stage of a line manufacturing process, including when the sample is obtained off-line from the manufacturing process after the fibrous product has been produced.

EXAMPLE

The invention will be further explained by the following illustrative example that is intended to be non-limiting.

Example 1

Extent of Binder Cure in Fiberglass Insulation

In order to determine the extent of binder cure in a manufactured fiberglass insulation product using the methods described herein, the fiberglass insulation was manufactured and then a sample of the fiberglass insulation was subjected to Fourier transform infrared spectroscopy (FTIR) as described below. The binder system used in the manufacture of the fiberglass was a polyacrylic acid resin and a triethanol amine.

Figure 2:
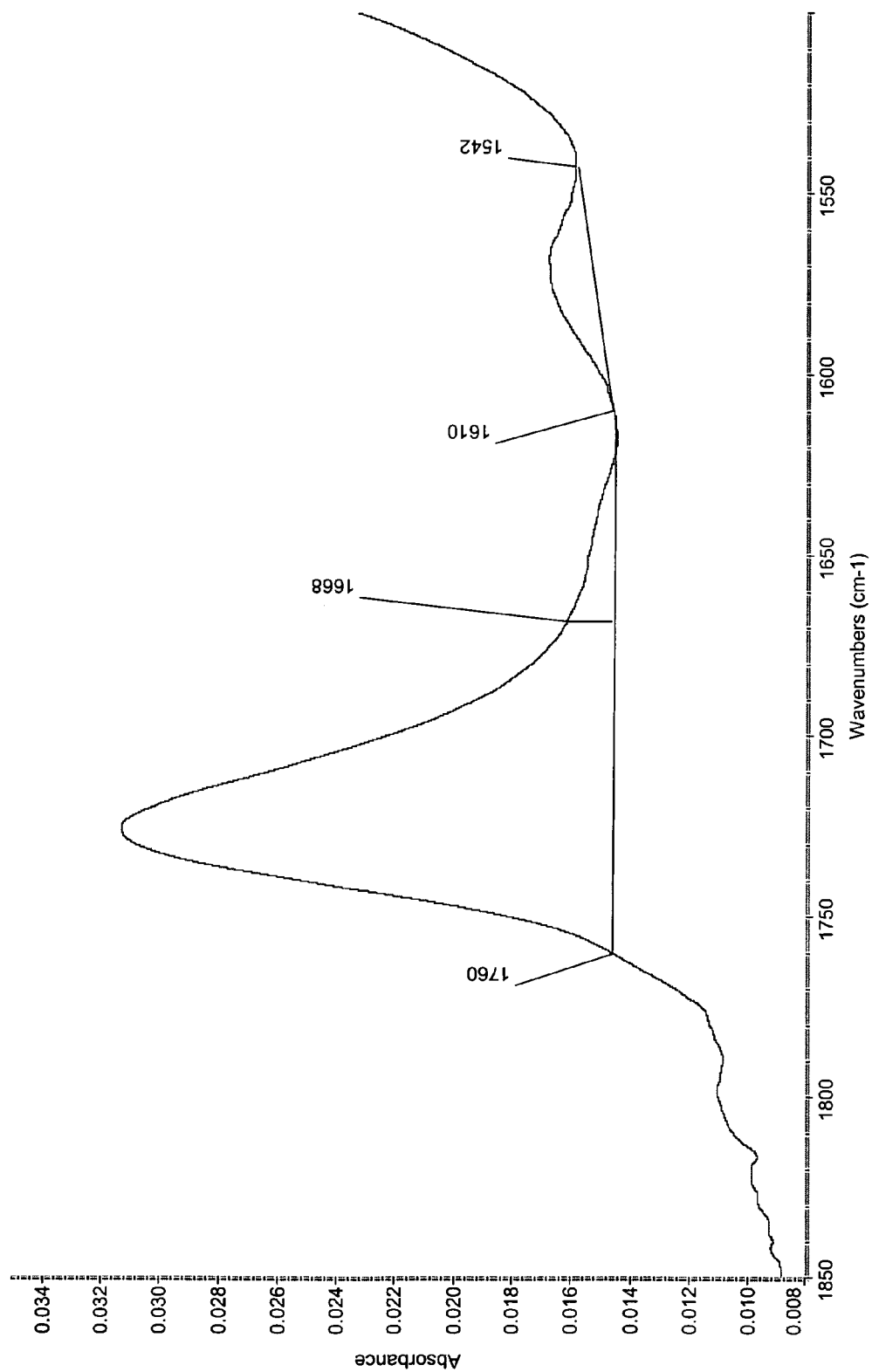
Figure 3:
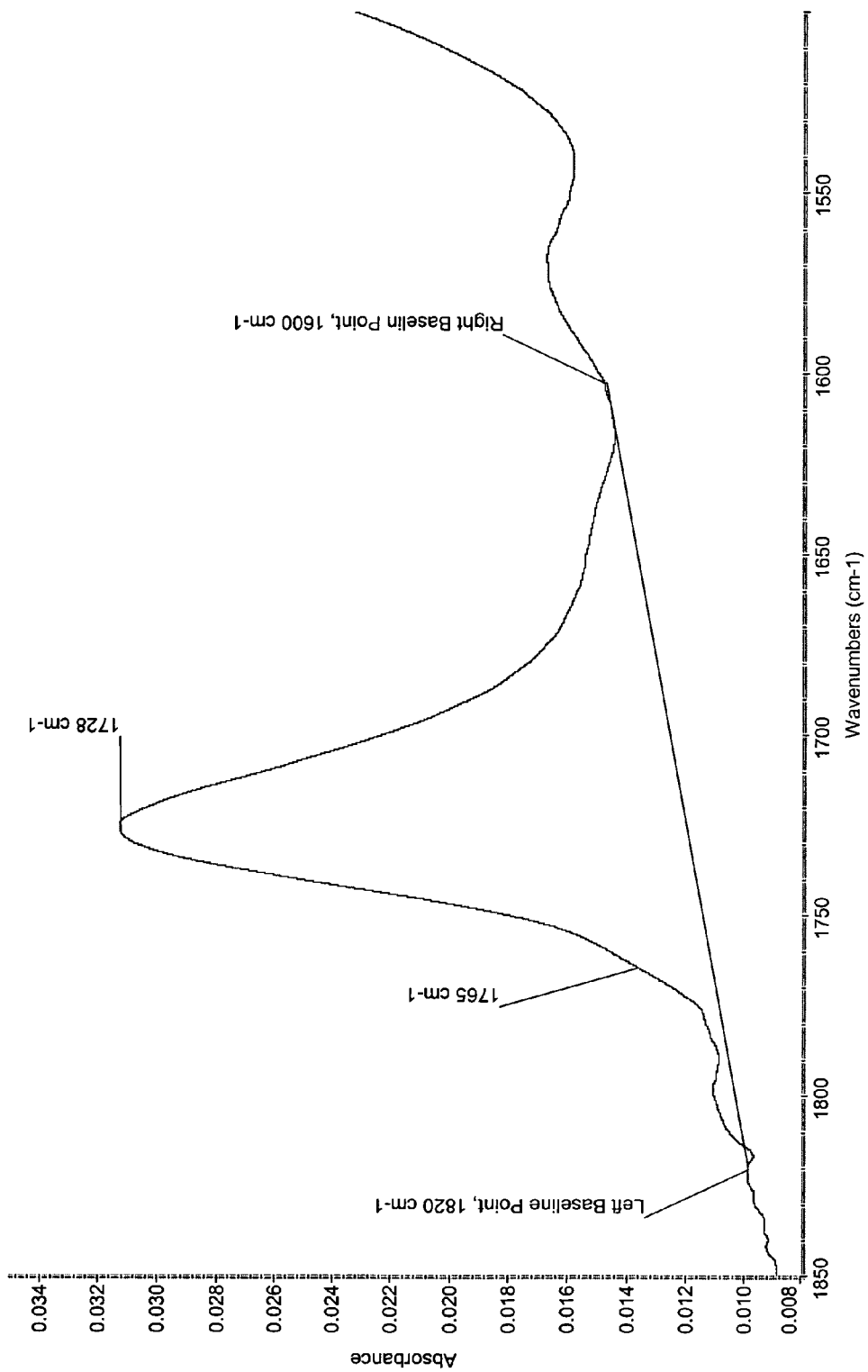

Shortly after manufacture, a portion of the fiberglass insulation product was homogenized using a grinding device. In order to generate a spectral analysis of the sample, the ground sample was subjected to FTIR using an attenuated total reflectance sampling device. FIGS. 1-3 illustrate the infrared spectrum obtained from the FTIR. As explained below, the infrared spectrum was then used to determine the binder cure ratio, the neutralization ratio (and percent neutralization), and anhydride ratio.

The binder cure ratio was calculated using the following formula, which was used to measure the infrared absorption of the carbonyl bond in the carboxylic acid groups of the binder and the carbonyl bond in the ester groups of the binder:

$$\text{Binder cure ratio} = \frac{\text{Baseline corrected absorbance at } 1700 \text{ cm}^{-1} \text{ (Acid)}}{\text{Baseline corrected absorbance at } 1745 \text{ cm}^{-1} \text{ (Ester)}}.$$

Using the formula, the binder cure ratio was determined to be 1.00.

FIG. 1 shows the frequencies that were measured to determine the binder cure ratio and also shows the baseline drawn between 1618 cm$^{-1}$ and 1810 cm$^{-1}$ used to correct the absorbances. As shown in FIG. 1, absorbances at 1700 cm$^{-1}$ and 1745 cm$^{-1}$ were used to measure the carbonyl bonds of the acid and ester, respectively. Because the absorption peaks for the carbonyl bond of the carboxylic acid and the carbonyl bond of the ester were not resolved, as shown in the FIG. 1, these frequencies (i.e., 1700 cm$^{-1}$ and 1745 cm$^{-1}$) were used in order to obtain minimal interference between peaks but still have sufficient sensitivity to the peak of interest.

The neutralization ratio was calculated using the following formula:

$$\text{Neutralization ratio}(R) = \frac{\text{Peak Area at } 1542 \text{ cm}^{-1} \text{ to } 1610 \text{ cm}^{-1} \text{ (acid salt)}}{\text{Peak Area at } 1668 \text{ cm}^{-1} \text{ to } 1760 \text{ cm}^{-1}}.$$

(total non-neutralized binder)

FIG. 2 shows the peak areas that were measured to determine the neutralization ratio and also shows a first baseline drawn between 1542 cm$^{-1}$ and 1610 cm$^{-1}$ and a second baseline drawn between 1668 cm$^{-1}$ and 1760 cm$^{-1}$ used to correct the peak areas. As shown in FIG. 2, the peak area at 1542 cm$^{-1}$ to 1610 cm$^{-1}$ was used to measure the absorption due to the carbonyl group of the acid salt. Peak area at 1668 cm$^{-1}$ to 1760. cm$^{-1}$ was used to measure the total absorption due to the carbonyl of the acid of the binder and the carbonyl of the ester of the binder (i.e., absorption due to binder that was not neutralized).

After the neutralization ratio (R) was calculated using the formula above, the percent neutralization of the polyacrylic acid binder was calculated using the following formula, which was determined using experimental titration data:

Percent neutralization=100*((k*R)+0.005)/(1.005+ (k*R)), where k=0.661 (as determined experimentally).

The percent neutralization was determined to be 4.57, which is an indicator of the level of carboxylic acid salts in the fiberglass insulation product. The neutralization of carboxylic acid groups in the polyacrylic acid binder could come from sodium hydroxide or other salts in the process water used to form the fiberglass insulation, from sodium leaching from the surface of the glass fibers, or possibly from the amine in the binder.

The anhydride ratio was calculated using the following formula:

$$\text{Anhydride ratio} = \frac{\text{Baseline corrected absorbance at } 1765 \text{ cm}^{-1} \text{ (anhydride)}}{\text{Baseline corrected absorbance at } 1728 \text{ cm}^{-1} \text{ (non-anhydride)}}.$$

Using the formula and the infrared spectrum, the anhydride ratio was determined to be 0.13, which is representative of the levels of binder in anhydride form compared to total levels of binder not in anhydride form.

FIG. 3 shows the frequencies that were measured to determine the anhydride ratio and also shows the baseline drawn between 1600 cm$^{-1}$ and 1820 cm$^{-1}$ used to correct the absorbances. As shown in FIG. 3, absorbance at 1765 cm$^{-1}$ was used to measure the absorption due to the carbonyl of the anhydride of the polyacrylic acid resin. Absorbance at 1728 cm$^{-1}$ was used to measure the total absorption due to the carbonyl of the acid of the binder and the carbonyl of the ester of the binder (i.e., absorption due to binder that was not in anhydride form).

After the binder cure ratio, percent neutralization, and anhydride ratio values were determined using the infrared spectrum, the values were compared to predetermined scales to measure the extent of cure of the binder in the fiberglass insulation. The predetermined scales were established to monitor the extent of cure for fiberglass insulation produced by the same method that was used to produce the sample in this example. The predetermined scales are listed below:

| Extent of Cure | Percent Neutralization | Acid/Ester FTIR Ratio (Binder Cure) | Anhydride Value |
|---|---|---|---|
| good | <1% | <0.9 | 0.1-0.3 |
| marginal | 1-3% | 0.9-1.0 | <0.1 |
| bad | >3% | >1.0 | |

The results show that the extent of cure for the sample was marginal in terms of acid to ester conversion and show that the sample had a high percent neutralization, which may have contributed to the marginal cure.

While the invention has been described in detail and with reference to specific embodiments thereof, it will be apparent to one skilled in the art that various changes and modifications can be made without departing from the spirit and scope of the invention.

What is claimed is:

1. A method of measuring the extent of cure of a binder in a fibrous product comprising:
   (a) providing a sample of a fibrous product, the fibrous product comprising fibers and a binder, the binder having carboxylic acid groups and alcohol groups that crosslink to form ester groups as the binder cures;
   (b) subjecting the sample to infrared spectroscopy to generate a spectral analysis;

(c) determining a binder cure ratio of the binder in the sample using the spectral analysis, the binder cure ratio comprising a ratio between infrared absorption corresponding to a bond of the carboxylic acid groups in the binder and infrared absorption corresponding to a bond of the ester groups in the binder, the binder cure ratio indicative of the extent of cure of the binder in the fibrous product.

2. The method of claim 1, further comprising comparing the binder cure ratio to a predetermined scale.

3. The method of claim 1, wherein the fibers are glass fibers.

4. The method of claim 1, wherein the binder comprises a polyacrylic acid and a polyol.

5. The method of claim 1, wherein the binder cure ratio comprises a ratio between infrared absorption corresponding to the C═O bond of the carboxylic acid groups in the binder and infrared, absorption corresponding to the C═O bond of the ester groups in the binder.

6. The method of claim 1, wherein the sample of fibrous product is obtained from a fibrous product produced by a line manufacturing process, the sample being obtained off-line from the manufacturing process after the product has been produced.

7. The method of claim 6, further comprising adjusting process conditions of the manufacturing process based on the determined extent of cure of the fibrous product.

8. The method of claim 1, wherein the sample of fibrous product is ground before being subjected to infrared spectroscopy.

9. The method of claim 1, wherein the infrared spectroscopy is Fourier transform infrared spectroscopy.

10. The method of claim 9, wherein step (b) is performed with a Fourier transform infrared spectrometer with an attenuated total reflectance sampling device.

11. A method of measuring the extent of cure of a binder in a fibrous product comprising:
(a) providing a sample of a fibrous product, the fibrous product comprising fibers and a binder, the binder having carboxylic acid and alcohol groups that crosslink to form ester groups as the binder cures, the binder capable of being neutralized to an acid salt having a carboxylate group;
(b) subjecting the sample to infrared spectroscopy to generate a spectral analysis;
(c) determining a binder cure ratio of the binder in the sample using the spectral analysis, the binder cure ratio comprising a ratio between infrared absorption corresponding to a bond of the carboxylic acid groups in the binder and infrared absorption corresponding to a bond of the ester groups in the binder;
(d) determining a neutralization ratio of the binder in the sample using the spectral analysis, the neutralization ratio comprising a ratio between infrared absorption corresponding to a bond of the carboxylate groups in the acid salt of the binder and total infrared absorption corresponding to a bond of the carboxylic acid groups in the binder and a bond of the ester groups in the binder; and
(e) using the binder cure ratio and the neutralization ratio to determine the extent of cure of the binder in the fibrous product.

12. The method of claim 11, wherein step (e) comprises comparing the binder cure ratio and the neutralization ratio to a predetermined scale or scales to determine the extent of cure of the binder in the fibrous product.

13. The method of claim 11, wherein the binder cure ratio comprises a ratio between infrared absorption corresponding to the C═O bond of the carboxylic acid groups in the binder and infrared absorption corresponding to the C═O bond of the ester groups in the binder.

14. The method of claim 11, wherein the neutralization ratio comprises a ratio between infrared absorption corresponding to the C═O bond of the carboxylate groups in the acid salt of the binder and total infrared absorption corresponding to the C═O bond of the carboxylic acid groups in the binder and the C═O bond of the ester groups in the binder.

15. The method of claim 11, wherein the fibers are glass fibers.

16. The method of claim 11, wherein the binder comprises a polyacrylic acid and a polyol.

17. The method of claim 11, wherein the sample of fibrous product is obtained from a fibrous product produced by a line manufacturing process, the sample being obtained off-line from the manufacturing process after the product has been produced.

18. The method of claim 17, further comprising adjusting process conditions of the manufacturing process based on the determined extent of cure of the fibrous product.

19. The method of claim 11, wherein the sample of fibrous product is ground before being subjected to infrared spectroscopy.

20. The method of claim 11, wherein the infrared spectroscopy is Fourier transform infrared spectroscopy.

21. The method of claim 20, wherein step (b) is performed with a Fourier transform infrared spectrometer with an attenuated total reflectance sampling device.

22. A method of measuring the extent of cure of a binder in a fibrous product comprising:
(a) providing a sample of a fibrous product, the fibrous product comprising fibers and a binder, the binder having carboxylic acid and alcohol groups that crosslink to form ester groups as the binder cures, the binder capable of being neutralized to an acid salt having a carbaxylate group, the binder also capable of forming an anhydride having a carboxylic acid anhydride group;
(b) subjecting the sample to infrared spectroscopy to generate a spectral analysis;
(c) determining a binder cure ratio of the binder in the sample using the spectral analysis, the binder cure ratio comprising a ratio between infrared absorption corresponding to a bond of the carboxylic acid groups in the binder and infrared absorption corresponding to a bond of the ester groups in the binder;
(d) determining a neutralization ratio of the binder in the sample using the spectral analysis, the neutralization ratio comprising a ratio between infrared absorption corresponding to a bond of the carboxylate groups in the acid salt of the binder and total infrared absorption corresponding to a bond of the carboxylic acid groups in the binder and a bond of the ester groups in the binder;
(e) determining an anhydride ratio of the binder in the sample using the spectral analysis, the anhydride ratio comprising a ratio between infrared absorption corresponding to a bond in the carboxylic acid anhydride groups of the anhydride of the binder and total infrared absorption corresponding to a bond of the carboxylic acid groups in the binder and a bond of the ester groups in the binder; and
(f) using the binder cure ratio, the neutralization ratio, and the anhydride ratio to determine the extent of cure of the binder in the fibrous product.

23. The method of claim 22, wherein step (f) comprises comparing the binder cure ratio, the neutralization ratio, and the anhydride ratio to one or more predetermined scales to determine the extent of cure of the binder in the fibrous product.

24. The method of claim 22, wherein the binder cure ratio comprises a ratio between infrared absorption corresponding to the C═O bond of the carboxylic acid groups in the binder and infrared absorption corresponding to the C═O bond of the ester groups in the binder.

25. The method of claim 22, wherein the neutralization ratio comprises a ratio between infrared absorption corresponding to the C═O bond of the carboxylate groups in the acid salt of the binder and total infrared absorption corresponding to the C═O bond of the carboxylic acid groups in the binder and the C═O bond of the ester groups in the binder.

26. The method of claim 22, wherein the anhydride ratio comprises a ratio between infrared absorption corresponding to the C═O bond of the carboxylic acid anhydride groups in the anhydride of the binder and total infrared absorption corresponding to the C═O bond of the carboxylic acid groups in the binder and the C═O bond of the ester groups in the binder 27. The method of claim 22, wherein the fibers are glass fibers.

28. The method of claim 22, wherein the binder comprises a polyacrylic acid and a polyol.

29. The method of claim 22, wherein the sample of fibrous product is obtained from a fibrous product produced by a line manufacturing process, the sample being obtained off-line from the manufacturing process after the product has been produced.

30. The method of claim 29, further comprising adjusting process conditions of the manufacturing process based on the determined extent of cure of the fibrous product.

31. The method of claim 22, wherein the sample of fibrous product is ground before being subjected to infrared spectroscopy.

32. The method of claim 22, wherein the infrared spectroscopy is Fourier transform infrared spectroscopy.

33. The method of claim 32, wherein step (b) is performed with a Fourier transform infrared spectrometer with an attenuated total reflectance sampling device.

34. A method of measuring the extent of cure of a binder in a fiberglass insulation product comprising:

(a) providing a sample of a fiberglass insulation product, the product comprising glass fibers and a binder, the binder comprising a polyacrylic acid with carboxylic acid groups and a polyol with alcohol groups, the carboxylic acid groups and the alcohol groups crosslinking to form ester groups as the binder cures;

(b) subjecting the sample to Fourier transform infrared spectroscopy to generate a spectral analysis; and (c) determining a binder cure ratio of the binder in the sample using the spectral analysis, the binder cure ratio comprising a ratio between infrared absorption corresponding to the C═O bond of the carboxylic acid groups in the binder and infrared absorption corresponding to the C═O bond of the ester groups in the binder, the binder cure ratio indicative of the extent of cure of the binder in the fiberglass insulation product.

35. The method of claim 34, further comprising comparing the binder cure ratio to a predetermined scale.

36. The method of claim 34, wherein step (b) is performed with a Fourier transform infrared spectrometer with an attenuated total reflectance sampling device.

37. The method of claim 34, further comprising determining a neutralization ratio of the binder from the spectral analysis and using the binder cure ratio along with the neutralization ratio to determine the extent of cure of the binder in the fiberglass insulation product;
wherein the neutralization ratio of the binder comprises a ratio between infrared absorption corresponding to the C═O bond of carboxylate groups in an acid salt of the binder and total infrared absorption corresponding to the C═O bond of the carboxylic acid groups in the binder and the C═O bond of the ester groups in the binder.

38. The method of claim 37, further comprising determining an anhydride ratio of the binder from the spectral analysis and using the binder cure ratio along with the neutralization ratio and anhydride ratio to determine the extent of cure of the binder in the fiberglass insulation product;
wherein the anhydride ratio of the binder comprises a ratio between infrared absorption corresponding to the C═O bond of carboxylic acid anhydride groups in an anhydride of the binder and total infrared absorption corresponding to the C═O bond of the carboxylic acid groups in the binder and the C═O bond of the ester groups in the binder.

* * * * *